United States Patent [19]
Karg

[11] Patent Number: 5,267,964
[45] Date of Patent: Dec. 7, 1993

[54] FLUID CONTROL DEVICE INCLUDING AUTOMATIC VALVE

[75] Inventor: Jeffrey Karg, Waldwick, N.J.
[73] Assignee: Clintec Nutrition Co., Deerfield, Ill.
[21] Appl. No.: 855,909
[22] Filed: Mar. 23, 1992
[51] Int. Cl.$^5$ ............................................. A61M 1/00
[52] U.S. Cl. ..................................... 604/141; 604/151
[58] Field of Search ................ 604/153, 153, 141, 151

[56] References Cited

U.S. PATENT DOCUMENTS

| | | |
|---|---|---|
| 2,941,544 | 6/1960 | Peras . |
| 4,043,332 | 8/1977 | Metcalf .............................. 604/141 |
| 4,210,173 | 7/1980 | Choksi . |
| 4,252,116 | 2/1981 | Genese et al. . |
| 4,299,220 | 11/1981 | Dorman .............................. 604/141 |
| 4,411,603 | 10/1983 | Kell . |
| 4,471,623 | 5/1949 | Hubbell . |
| 4,508,136 | 4/1985 | Kah, Jr. . |
| 4,573,888 | 3/1986 | Kitchin . |
| 4,634,430 | 1/1987 | Polaschegg ........................ 604/141 |
| 4,646,781 | 3/1987 | McIntyre et al. . |
| 4,666,429 | 5/1987 | Stone . |
| 4,673,391 | 6/1987 | Kondo et al. ....................... 604/141 |
| 4,769,012 | 9/1988 | Quang et al. . |
| 4,813,927 | 3/1989 | Morris et al. ...................... 604/141 |
| 4,846,636 | 7/1989 | Danby et al. . |
| 4,898,581 | 2/1990 | Iwatschenko . |
| 4,904,243 | 2/1990 | Bruera . |
| 4,946,448 | 8/1990 | Richmond . |
| 4,955,860 | 9/1990 | Ruano ................................ 604/141 |
| 5,025,829 | 6/1991 | Edwards et al. . |
| 5,066,282 | 11/1991 | Wijay et al. . |
| 5,070,905 | 12/1991 | Paradis . |
| 5,176,658 | 1/1993 | Ranford . |

FOREIGN PATENT DOCUMENTS

| | | |
|---|---|---|
| 2639-992 | 9/1976 | Fed. Rep. of Germany . |
| 2649-813 | 10/1976 | Fed. Rep. of Germany . |
| 3503-320 | 1/1985 | Fed. Rep. of Germany . |
| 3518575 | 4/1985 | Fed. Rep. of Germany . |
| WO87/00758 | 2/1987 | PCT Int'l Appl. . |
| WO88/02639 | 4/1988 | PCT Int'l Appl. . |
| WO89/02764 | 4/1989 | PCT Int'l Appl. . |
| WO90/12609 | 11/1990 | PCT Int'l Appl. . |
| 9108002 | 6/1991 | PCT Int'l Appl. . |
| 9300944 | 1/1993 | PCT Int'l Appl. . |

*Primary Examiner*—Paul J. Hirsch
*Attorney, Agent, or Firm*—Hill, Steadman & Simpson

[57] ABSTRACT

A fluid delivery device and method of delivering fluid is provided. The device comprises a delivery member including a member for creating a vacuum pressure, to suck fluid into a reservoir, and for expelling fluid from the reservoir. A body is provided including a first opening, a second opening, and a third opening, the interior of the body defining a first fluid pathway from the first opening to the second opening and a second fluid pathway from the second opening and a second fluid pathway from the second opening to the third opening. The delivery member is coupled to the second opening. A fluid source is coupled to the first opening. A fluid conduit is coupled to the third opening for allowing the device to deliver product to a patient. The first and second fluid pathways are defined in part by walls that define a central cavity and a diaphragm located therein. The diaphragm closing both the first and second fluid pathways when it is in a first, static position and opening the first pathway when the delivery member creates a vacuum pressure, while maintaining the second pathway in a closed position. When the delivery member creates a positive pressure, the second pathway is opened while the first fluid pathway is maintained in a closed position.

20 Claims, 3 Drawing Sheets

FLUID CONTROL DEVICE INCLUDING AUTOMATIC VALVE

BACKGROUND OF THE INVENTION

The present invention relates generally to devices for controlling the flow of fluids. More specifically, the present invention relates to fluid delivery devices.

It is known in the medical industry to administer to a patient a fluid. The fluid can be administered parenterally or enterally to the patient. Examples of some parenteral fluids include blood and blood fractions, sugar, electrolytes, osmotic solutions, and nutrient preparations. Many beneficial and therapeutic agents are delivered parenterally to avoid the digestive tract and liver.

Of course, it is known to administer directly to a patient an intravenous fluid through a drip method. To this end, an intravenous container or bag is coupled to a patient by use of a fluid conduit or tube that terminates in a needle. The needle is inserted in the patient and the bag is hung at an elevated position. Fluid then flows from the container into the patient.

A number of devices are utilized in order to control the fluid flow into the patient. These fluid flow devices can include a roller clamp which is used to restrict the diameter of the tube limiting the fluid flow through the tube into the patient.

In many situations and with certain drugs, it is necessary to exactly regulate and control the flow of drug into the patient. With certain drugs and/or patients, if the flow rate of the drugs is not accurately controlled, a beneficial agent can have severe adverse consequences on a patient. In these situations, it is not possible merely to allow the fluid to flow directly from the container into the patient, but rather, some type of infuser mechanism is necessary.

A number of such infusers are known. For example, it is known to use infusion pumps, that may include a peristaltic pump, to control the flow of the fluid through the conduit to the patient.

It is also known to utilize with infusion pumps manually actuated devices that must be manually controlled in order to regulate fluid flow into the patient.

SUMMARY OF THE INVENTION

The present invention provides a fluid device. In an embodiment, the device of the present invention, allows fluid to flow from a fluid source, through a first fluid pathway into a delivery means and then from the delivery means into a patient via a second fluid pathway. The device automatically opens and closes the necessary fluid pathways to prevent: a reverse flow of fluid from the patient into the delivery means; a reverse flow of fluid from the delivery means into the fluid source; a reverse flow of fluid from the patient into the fluid source; and a direct flow of fluid from the fluid source into the patient.

To this end, the present invention provides a delivery device comprising a fluid source coupled to a body having a first opening. A delivery means is provided including means for creating a vacuum pressure, to allow the delivery means to receive a fluid, and for creating a positive pressure, to expel a fluid from the delivery means, the delivery means is coupled to the body at a second opening of the body. The body includes a third opening that can be coupled to a fluid conduit for allowing the fluid to be delivered to a patient.

The body defines an interior having a first fluid pathway from the first opening to the second opening and a second fluid pathway from the second opening to the third opening. The body includes valve means that closes both the first and second fluid pathways in a first static position. Upon the exertion of a positive pressure by the delivery means, the valve means opens the second fluid pathway while maintaining the first fluid pathway in a closed position. In response to a vacuum pressure, created by the delivery means, the valve means opens the first fluid pathway and maintains the second fluid pathway in a closed position.

The construction of the body and valve means allows fluid to be received by the delivery means and administered to a patient. However, the device also prevents the "no flow" situations set forth above.

In an embodiment, a drug delivery device is provided comprising a motor driven syringe, including a barrel and a means for creating a vacuum pressure, to suck fluid into the barrel, and for expelling fluid from the barrel. A body is provided including a first opening, a second opening, and a third opening, the interior of the body defining a first fluid pathway from the first opening to the second opening and a second fluid pathway from the second opening to the third opening. The motor driven syringe is coupled to the second opening. A fluid source is coupled to the first opening. A fluid conduit is coupled to the third opening for allowing the device to deliver product to a patient. The first and second fluid pathways are defined in part by walls that define a central cavity and a diaphragm located therein. The diaphragm closing both the first and second fluid pathways when it is in a first, static position and opening the first pathway when the motor driven syringe creates a vacuum pressure, while maintaining the second pathway in a closed position. When the motor driven syringe creates a positive pressure, the second fluid pathway is opened while the first fluid pathway is maintained in a closed position.

The present invention also provides a method for delivering a fluid to a patient comprising the steps of: providing a fluid source; providing a body having a first opening, a second opening, and a third opening; coupling the fluid source to the first opening; coupling a delivery device to the second opening; coupling a fluid conduit to the third opening; causing fluid to flow only from the fluid source to the delivery device upon exertion of a vacuum pressure by the delivery device; and causing fluid to flow from the second opening to only the third opening upon exertion of a positive pressure by the delivery device.

The present invention allows decreased drug delivery pressures to be utilized to deliver product to a patient than used in some prior devices. Further, the present invention allows an increase in the direct bag to patient delivery to greater than the bag burst strength. Further, the present invention decreases syringe fill pressures so as to reduce nurse fatigue.

As discussed in detail below, the present invention provides a new valve employing a diaphragm that acts as a switching device. Pursuant to the present invention, either the syringe can accept medication from a fluid source or can deliver medication to the patient. At no time can medication pass from the fluid source to the syringe to the patient in any direction or combination, unless the syringe is activated. The syringe is the only activation device. Neither the fluid source nor the patient can cause medication flow.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an automatic delivery system and method for same. The system allows medication to be drawn into a syringe, or infusion pump, automatically upon the creation of a vacuum, e.g., by pulling outwardly the plunger. Upon expelling the fluid from the syringe, or pump, e.g., pushing the plunger in, the system allows the medication to be delivered to the patient. Automatic means are provided by the present invention which do not require buttons or levers to be actuated to switch from a syringe load to a syringe deliver mechanism.

Although, as described in the presently preferred embodiment, a motor driven syringe is used to deliver the medication to a patient, other delivery means can be utilized, e.g., an infusion pump. Such means merely need to create a vacuum and then to exert a sufficient force to force the fluid contained within the delivery means through a fluid line into a patient.

Additionally, although as set forth in detail below, a preferred embodiment of the present invention is for use in delivering medical fluid to a patient, the present invention can be used to deliver most any fluid in a variety of fields. Furthermore, the present invention can also be used to control fluid flow, i.e., as a valve switch, and need not be limited to a fluid delivery device.

Figure 1:
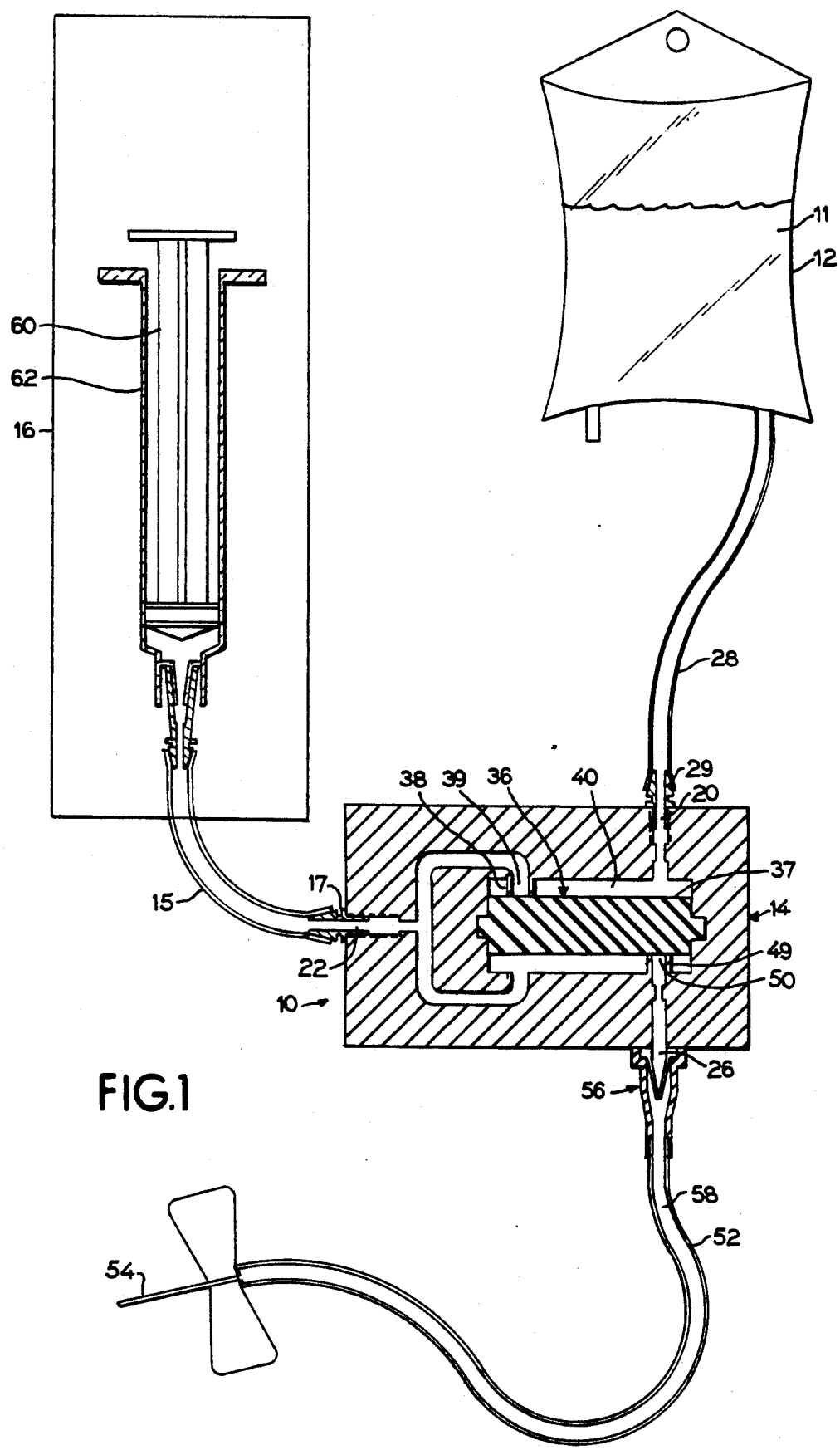
FIG. 1 illustrates a cross-sectional, schematic view, of the device of the present invention in a first static position.

Referring now to the Figures, as illustrated in FIG. 1, the device 10 is utilized to deliver a fluid 11 contained within, for example, a bag 12 to a patient. This fluid can be a drug or fluid that is to be administered directly to a patient, admixed with another fluid or drug, or used for reconstituting a powdered drug.

Because the device 10 in the illustrated embodiment is designed to be used as a device for accurately delivering drugs or fluid to a patient, there are four required "no-flow" conditions that must be met by the device:
1) there can be no reverse flow of fluid from the patient into the delivery means (e.g., syringe);
2) there can be no reverse flow of fluid from the delivery means into the fluid source (e.g., bag);
3) there can be no reverse flow of fluid from the patient into the fluid source; and
4) there can be no direct flow of fluid from the fluid source into the patient.

The device 10 of the present invention fulfills all of the above requirements.

To this end, the device provides a body 14 that in addition to being coupled to a fluid source 12, is also coupled to a delivery means, in the illustrated embodiment, a motor driven syringe 16, and a patient. As discussed in detail below, the device 10 allows fluid to be received within the motor driven syringe 16 and expelled from the syringe 16 to the patient. In the preferred embodiment illustrated, the syringe 14 is coupled to the body by a fluid conduit 15 and luer connector 17.

The body 14 includes a first opening 20, a second opening 22, and a third opening 26. The first opening 20 is coupled to the fluid source 12. In the embodiment illustrated, the fluid source 12 is coupled to the first opening 20 by a tubing 28 that terminates in a luer connector 29.

Figure 2:
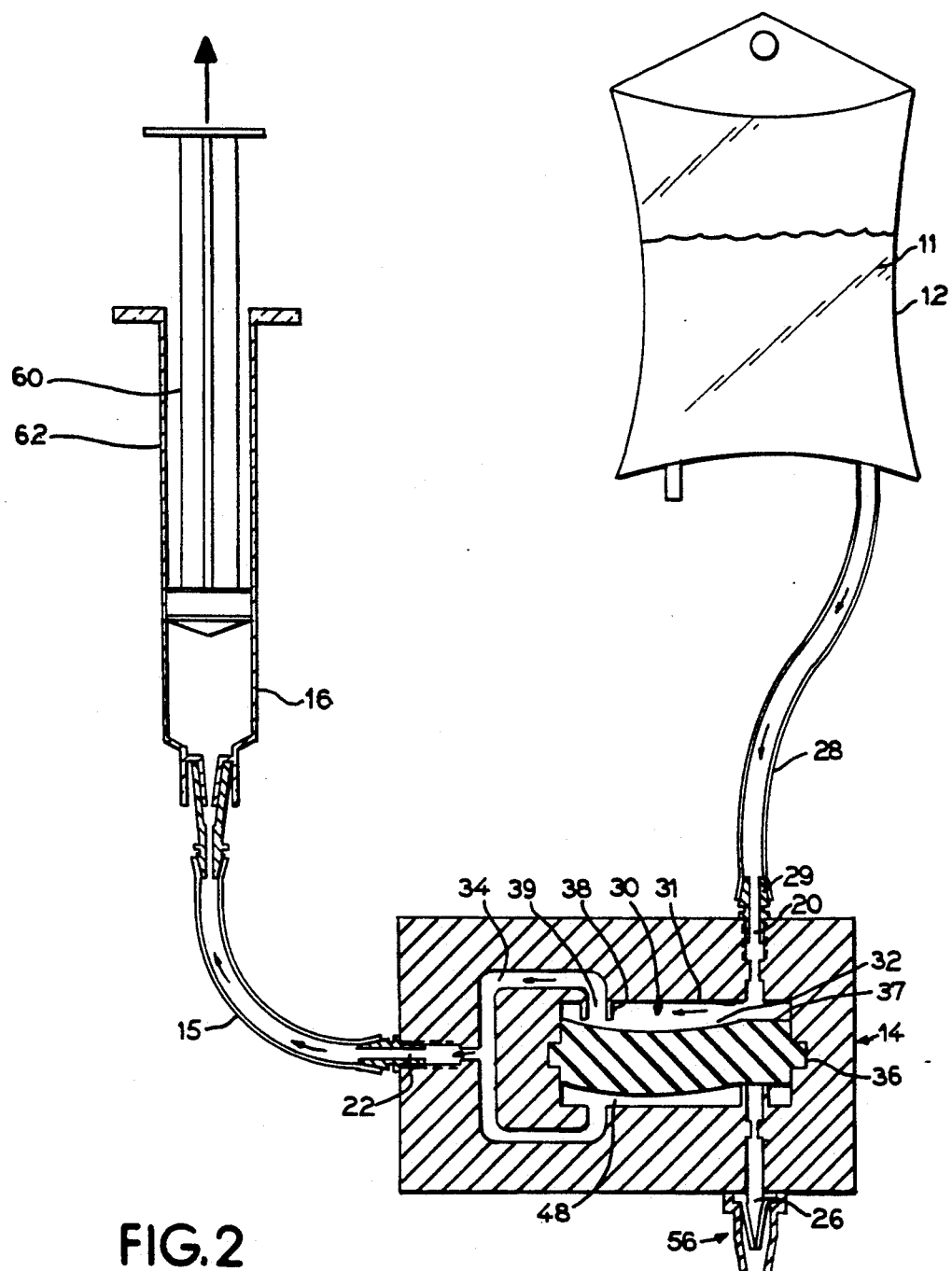
FIG. 2 illustrates a cross-sectional view of the device of FIG. 1 in a syringe fill position.

When the device 10 is in the position illustrated in FIG. 2, the first opening 20 is in fluid communication with the second opening 22 through a first flow path 30. The first flow path 30 is defined by the first inlet 20, a portion of an internal wall 31 that defines a central cavity 32, and a first channel 34 that terminates in juxtaposition to the second inlet 22. Additionally, a diaphragm member 36 located in the central cavity 32, and specifically a top portion 37 thereof, defines, in part, the first fluid flow path 30.

As illustrated, the first channel 34 includes an extended portion that is essentially a truncated tube 38 including an opening 39 that extends into an upper portion 40 of the central cavity 32. In the static position of the device illustrated in FIG. 1, i.e., when no pressure (either positive or negative) is being exerted by the syringe 16, the first flow path 30 is closed. This is due to the diaphragm member 36 that is biased against the opening 39 of the truncated tube 38.

The body 14 also defines a second fluid flow path 42 from the second opening 22 to the third opening 26; the third opening 26 functions as an outlet. The second fluid flow path 42 is defined, in part, by a second channel member 44, the interior wall 45 of the body that defines a lower section 46 of the central cavity 32, and a bottom 48 of the diaphragm member 36.

As illustrated, the third opening 26 includes an extended channel 47 extending from the third opening 26 into the lower section 46 of the central cavity 32. The channel 47 defines a second truncated tube 49 that terminates in an opening 50. In the static position, illustrated in FIG. 1, the diaphragm 36 also closes the opening 50 of the second truncated tube 49.

In the static position, the syringe 16 is not exerting either a vacuum or positive pressure. In the static position, fluid flow is prevented from the fluid source 12 to either the syringe 16 or patient. Likewise, fluid flow is prevented from the syringe 16 to the patient or the fluid source 12.

As illustrated in FIG. 1, a fluid conduit or tube 52 extends from the third opening 26 to a patient (not shown). The fluid conduit 52 can terminate in a needle 54 to allow the fluid to be intravenously administered to a patient. In an embodiment, the fluid conduit 52 includes a duckbill valve 56 to prevent fluid from flowing from an interior 58 of the fluid conduit 52 into the body 14. The duckbill valve 56 functions as a one way valve to allow fluid to flow from the device 10 to a patient and not vice versa. The one way valve, if desired, can be located at other positions in the device, for example, in the second channel member 44.

Referring now to FIG. 2, the motor driven syringe 16, or delivery means, fill position is illustrated. As illustrated, a vacuum force is being exerted by the syringe 16. To this end, the plunger member 60 is pulled in a direction (indicated by the arrow) out of the barrel 62 creating a suction force. Due to the construction of the body 14, the suction force pulls the diaphragm 36 down.

This opens the first fluid pathway 30, causing fluid flow as indicated by the arrow, while maintaining the second fluid pathway 42 in a closed position.

The diaphragm 36 provides an automatic valve means in response to the pressure exerted by the syringe 16 due to the body 14. To this end, the diaphragm 36 is constructed from an elastomer. Any number of medical grade elastomers can be used. Preferably, the material has a durometer reading in the range of 10–60 Shore A. It has been found that a silicone available from Dow Chemical under the designation Q7-4840 functions satisfactorily.

The thickness of the diaphragm 36 can vary. Preferably, the thickness is in the range of approximately 0.04 inches to 0.2 inches. A thickness of 0.1 inch has been found to function satisfactorily.

Further, although the diaphragm 36 can be almost any shape, in the illustrated embodiment, the diaphragm is a circle having a 1 inch diameter. Correspondingly, the openings 39 and 59 have an approximately 0.1 inch diameter.

To create the automatic valve means in response to the pressure of the syringe 16, the interior of the body 14 is constructed so that a greater surface area of the bottom 48 of the diaphragm member 36 is exposed to the pressure exerted by the syringe 16, or other pump means, than a top portion 37 of the diaphragm member 36.

The inventors believe that the total surface area of the bottom 48 of the diaphragm 36 vis-a-vis the surface area of the top 37 of the diaphragm exposed to the pressure exerted by the syringe, needs only to be greater, in certain circumstances, in order to achieve the automatic valve means. The ratio will depend on the thicknesses of the diaphragm 36, the elastic characteristics of the diaphragm 36, and the fluid used. Preferably, the ratio of surface areas exposed to fluid communication with the delivery means is at least 2 to 1.

In the preferred embodiment illustrated, only a small portion of the top 37 of the diaphragm 36, that portion that covers the first truncated tube 38, is in fluid communication with the syringe 16 when the diaphragm 36 is in the static position. In contrast, substantially the entire surface area of the bottom portion 48 of the diaphragm 36, except the portion 63 that covers the opening 50 of the second truncated tube 48, is in fluid communication with the syringe 16 when the device 10 is in the static position.

Due to the construction of the device 10, even a minimal vacuum force will cause the diaphragm 36 to move downwardly, opening the first fluid flow path 30. Likewise, even a minimal pressure exerted by the syringe 16 will cause the second fluid flow path 42 to open. In the preferred embodiment illustrated, it has been found that a 100/1 ratio of the bottom portion 48 of the diaphragm 36 to the top portion 37 of the diaphragm 36 that is in fluid communication with the syringe 16 when it is in a static position, functions satisfactorily. However, a greater or lesser surface area ratio can be used.

As illustrated in FIG. 2, when the first fluid flow path 30 is opened, fluid can be pulled from the bag 12 into the syringe 16. At the same time, however, the diaphragm 36 closes the second fluid path 42. This prevents any fluid from directly flowing from the bag 12 into the patient.

Figure 3:
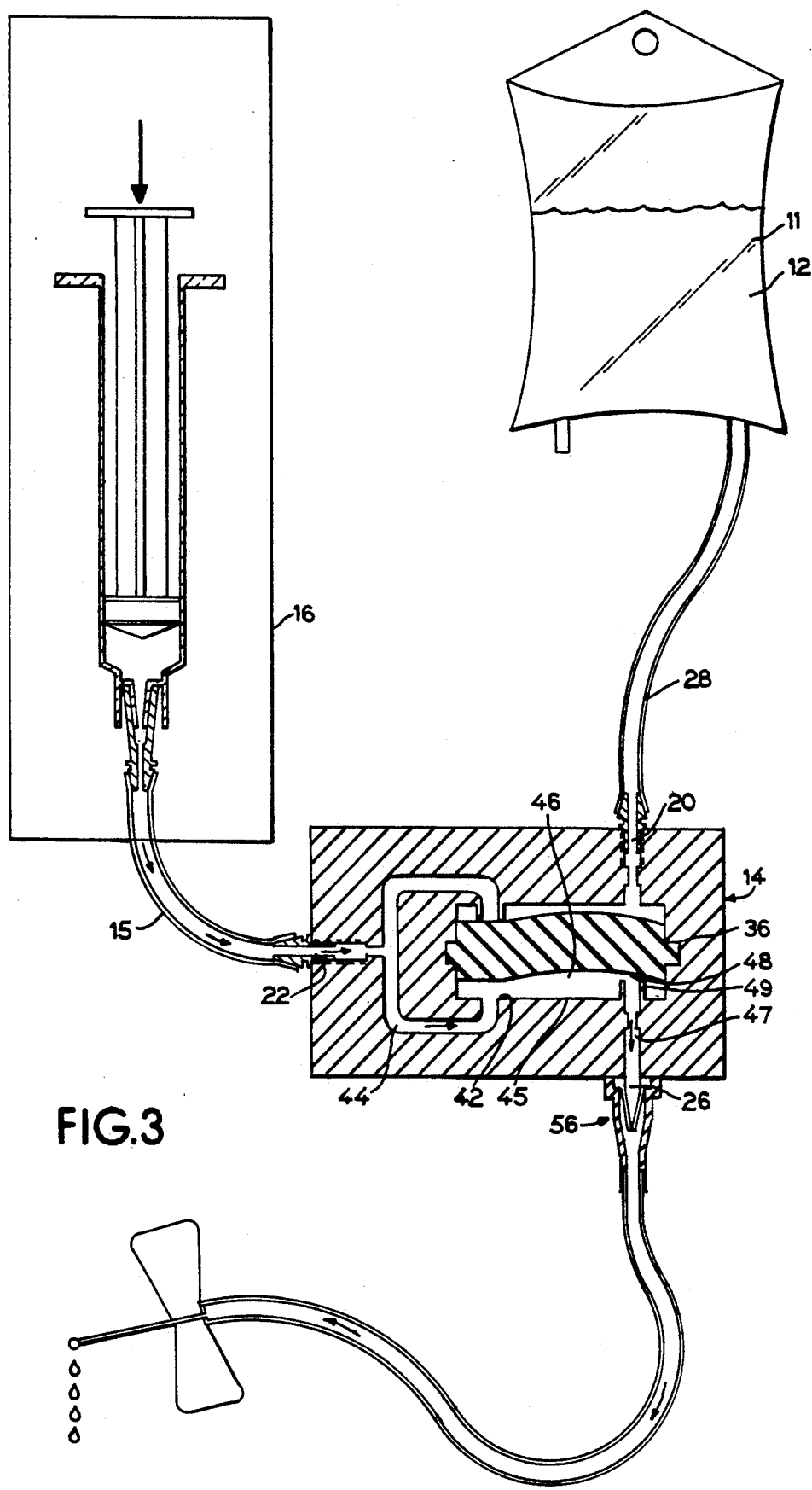
FIG. 3 illustrates a cross-sectional view of the device of FIG. 1 in a patient delivery mode.

FIG. 3 illustrates the patient delivery mode of the device 10 of the present invention. In this mode, the motor driven syringe 16 creates a positive pressure by the plunger 60 being forced into the barrel 62 of the syringe causing fluid to flow into the body 14 and specifically into the first channel 34 and second channel 44. Again, due to the larger surface area of the bottom portion 48 of the diaphragm 3 that is exposed to fluid communication with the fluid expelled from the motor driven syringe 16, the diaphragm member 36 is forced upwardly continuing to seal off the first fluid flow pathway 30 while opening the second fluid flow pathway 42.

In the patient delivery mode, fluid can flow (as indicated by the arrow) through the second fluid flow pathway 42 from the syringe 16 into the fluid delivery conduit 52 and thereby the patient. The device 10 allows sufficient pressure to be exerted by the motor driven syringe 16 to overcome the duckbill valve 56. In some infusion devices, the pressure necessary to overcome a one-way valve located between a device and the patient is too great causing the infusion pump alarm to activate and the pump to stop drug delivery. The present invention overcomes this difficulty.

Accordingly, the present invention provides a device that automatically chooses the correct fluid flow pathway to insure that the motor driven syringe 16 can be filled without a patient receiving fluid directly from the bag 12 and allows the fluid to be infused into a patient without infusing the fluid back into the bag.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A fluid control device comprising:
   a fluid source coupled to a manifold having a first opening;
   a delivery means including means for creating a vacuum pressure and a positive pressure and including a member for receiving a fluid, the delivery means being coupled to the body at a second opening of the manifold;
   a fluid conduit coupled to a third opening of the manifold; and
   the manifold defining in an interior thereof, a first fluid path from the first opening to the second opening and a second fluid path from the second opening to the third opening, the manifold including a diaphragm for fluidly closing both the first fluid path and the second fluid path when the diaphragm is in a first static position and automatically allowing fluid flow through the first fluid path upon the exertion of a vacuum pressure by the delivery means and for allowing fluid flow through the second fluid path upon the exertion of a positive pressure by the delivery means.

2. The fluid control device of claim 1 wherein the delivery means includes a syringe.

3. The fluid control device of claim 1 wherein the fluid conduit includes a one-way valve.

4. A fluid delivery device comprising:
   delivery means, including a fluid receiving reservoir and a means for creating a vacuum pressure to suck fluid into the fluid receiving reservoir and for expelling fluid from a body;

the body including a first opening, a second opening, and a third opening, the body defining a first fluid path from the first opening to the second opening and a second fluid path from the second opening to the third opening, the first and second fluid paths being defined in part by a central cavity and a diaphragm located therein the diaphragm being so constructed and arranged that it fluidly closes both fluid pathways in a first static position, opens the second fluid path when the delivery means creates a positive pressure and opens the first fluid path when the delivery means creates a vacuum pressure;

the delivery means being coupled to the second opening;

a fluid source coupled to the first opening; and a fluid conduit coupled to the third opening.

5. The fluid delivery device of claim 4 wherein the diaphragm includes a top portion and a bottom portion, the top portion defining a part of the first fluid path and the bottom portion defining a part of the second fluid path, the body being so constructed and arranged that a greater surface area of the bottom portion is in fluid communication with the delivery means than a surface area of the top portion when the device is in the first static position.

6. The fluid delivery device of claim 4 wherein the fluid conduit includes a one-way valve preventing fluid flow from an interior of the fluid conduit into the body.

7. The fluid delivery device of claim 4 wherein:

the first fluid path includes a first channel from the central cavity to the second opening, the first channel including a truncated tube portion that extends into the central cavity.

8. The fluid delivery device of claim 4 wherein the delivery device is a motor driven syringe.

9. The fluid delivery device of claim 4 wherein the fluid source is a container of medical fluid.

10. The fluid delivery device of claim 4 wherein the third opening includes a channel that extends into the central cavity and includes a truncated tube portion.

11. The fluid delivery device of claim 5 wherein the ratio of surface area of the bottom portion of the diaphragm that is in fluid communication with the delivery device as compared to the surface area top portion is at least approximately 2 to 1.

12. A drug delivery device comprising:

a fluid source coupled to a first opening of a body;

an infusion pump coupled to a second opening of a body;

the infusion pump capable of creating a vacuum pressure and a positive pressure;

a fluid conduit coupled to a third opening of the body;

the manifold including a central cavity divided into an upper and lower portion by a diaphragm, the diaphragm preventing at all times fluid flow directly between the upper and lower portions;

when the device is in a fill mode, the body defining a first fluid flow path from the first opening to the second opening, the first fluid flow path being defined, at least in part, by an upper wall of the central cavity and a top surface of the diaphragm;

when the device is in a delivery mode, the body defining a second fluid flow path from the second opening to the third opening, the second fluid path being defined, at least in part, by the lower wall of the central cavity and a bottom surface of the diaphragm; and the body and diaphragm being so constructed and arranged that the fill mode is automatically achieved by creating a vacuum pressure with the infusion pump, and the delivery mode is automatically achieved by creating a positive pressure with the infusion pump.

13. The drug delivery device of claim 12 wherein the infusion pump includes a syringe.

14. The drug delivery device of claim 12 wherein the third opening includes a channel that extends into the central cavity and includes a truncated tube portion.

15. The drug delivery device of claim 12 wherein the ratio of surface area of the bottom surface of the diaphragm is in fluid communication with the infusion pump as compared to the top surface of the diaphragm is at least approximately 2 to 1.

16. The drug delivery device of claim 12 wherein the fluid conduit includes a one-way valve to prevent fluid flow from an interior of the fluid conduit into the body.

17. The drug delivery device of claim 12 wherein the first and second fluid flow paths are defined, in part, by first and second channels, respectively, the first and second channels being in fluid communication with each other.

18. A method for delivering a fluid to a patient comprising the steps of:

providing a fluid source;

providing a body having a first opening, a second opening, and a third opening coupling the fluid source to the first opening;

coupling a delivery means to the second opening;

coupling a fluid conduit to the third opening;

providing a diaphragm for preventing fluid flow from the fluid source to the delivery means and from the second outlet to the third opening when the diaphragm is in a first static position;

causing fluid to flow only from the fluid source to the delivery means upon exertion of a vacuum pressure by the syringe; and causing fluid to flow from the second outlet to only the third opening upon exertion of a positive pressure by the syringe.

19. The method of claim 18 including the step of preventing fluid from flowing from the fluid conduit into the body.

20. The method of claim 18 including the step of placing a medicament in the fluid source.

* * * * *